United States Patent [19]

Mehta

[11] 4,347,176
[45] Aug. 31, 1982

[54] COMPOUNDS AND METHODS OF MAKING SAME

[75] Inventor: Nariman B. Mehta, Raleigh, N.C.

[73] Assignee: Burroughs Wellcome Co., Research Triangle Park, N.C.

[21] Appl. No.: 140,157

[22] Filed: Apr. 14, 1980

[51] Int. Cl.³ ............... C07G 7/00; C07C 69/527; C07C 101/30; G01N 33/54

[52] U.S. Cl. ................ 260/112 B; 560/39; 560/193; 424/1; 424/12; 23/230 B

[58] Field of Search ............... 424/1, 12; 435/7; 23/230 B; 560/39, 193; 422/61

[56] References Cited

U.S. PATENT DOCUMENTS 4,041,076  8/1977  Avenia ........................ 424/1
4,120,867  10/1978  Akerkar et al. ............... 560/39

OTHER PUBLICATIONS

Findlay et al., Res. Comm. Chem. Pathol. Pharmacol., 17(4), 595-603 (1977).

Primary Examiner—Christine M. Nucker
Attorney, Agent, or Firm—Donald Brown

[57] ABSTRACT

A radioimmunoassay procedure has been discovered for bupropion [(±)-2-t-butylamino-3-chloropropiophenone], an antidepressant compound, in biological fluids. Novel compounds of formula

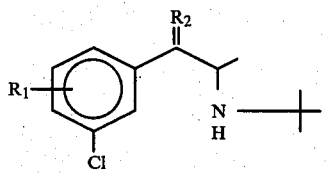

wherein either $R_2$ is oxygen and $R_1$ is $(CH_2)_n$—O—(CO)$_m$—(CH_2)_p$—COOH where n is an integer from 0 to 5, m is 0 or 1, and p is an integer from 1 to 4; or $R_1$ is hydrogen and $R_2$ is N—O—$(CH_2)_q$—COOH where q is an integer from 1 to 3, and novel methods of making them and novel intermediates useful therein are disclosed. Novel immunogens for raising bupropion specific antisera, and novel methods of making them are disclosed comprising conjugates of the novel compounds and suitable carrier material. The drug is added to the antisera together with novel radiolabeled competitor of formula wherein R' is a suitable radioisotope as described above and $R_3$ is hydrogen, $R_4$ is Cl, and $R_5$ is oxygen, or
  R' is hydrogen and either
  (a) $R_3$ is H and $R_4$ is Cl and $R_5$ is NO$(CH_2)_q$CO—X where q is as defined for formula I and X is a group having formula III wherein $R_6$ is a suitable radioisotope as described above, $R_7$ is hydroxyl, and s is an integer from 1 to 4;
  (b) $R_4$ is Cl, $R_5$ is oxygen, and $R_3$ is $(CH_2)_n$—O—(CO)-$_m$—(CH_2)_p$—CO—X where n, m, and p are as defined for formula I and X is as defined above; or
  (c) $R_3$ is hydroxy, $R_5$ is oxygen and $R_4$ is a suitable radioisotope as defined above.

The measure of radioactivity of the antisera bound radiolabeled competitor provides a measure of the amount of drug in the assayed biological fluid sample. A standard curve can be constructed from which the amount of drug in the assay sample can be interpolated. A kit is disclosed for practicing the radioimmunoassay.

18 Claims, 2 Drawing Figures

STANDARD CURVE OF EXAMPLE XI

CONCENTRATION (ng (free base)/ml)

COMPOUNDS AND METHODS OF MAKING SAME

BACKGROUND OF THE INVENTION

The present invention relates to a radioimmunoassay for clinical or experimental testing for the presence of and quantitation of bupropion [(±)-2-tert-butylamino-3′-chloropropiophenone], a pharmacologically active antidepressant compound, in biological fluids, including especially human sera or plasma.

The radioimmunoassay technique is finding increasing application for quantitation of drugs in biological fluids. Monitoring of plasma concentrations of drugs enables more precise dose administration to ensure efficacy. In the hospital laboratory setting, specific radioimmunoassay methods can offer considerable advantages such as improved sensitivity and specificity and, particularly, greater speed and sample capacity, over the generally more laborious methods of gas chromatography or thin-layer chromatography.

Accordingly, it is a purpose of the present invention to provide a radioimmunoassay procedure to determine the presence and concentration of bupropion in biological fluids, especially human sera or plasma.

It is another purpose of the invention to provide suitable radiolabeled agents for use in the radioimmunoassay.

It is another purpose of the invention to provide antibodies directed against bupropion also referred to as bupropion-specific antisera and as anti-bupropion sera. In this regard, it is a further purpose of the present invention to provide suitable immunogens for use to raise bupropion-specific antisera, and to provide methods suitable for raising such antisera.

Further purposes appear in the specification and in the claims.

The radioimmunoassay of the present invention is based on competition between bupropion and a fixed quantity of a distinguishable competitor of bupropion for a limited number of binding sites on bupropion-specific antibodies. The distinguishable competitor is preferably a labeled compound, such as a compound labeled with a radioactive isotope ("radiolabeled").

The drug and its radiolabeled competitor are added to the antibodies and the reaction mixture is allowed to equilibrate. When the antibody-bound portion is separated from the free drug and free radiolabeled competitor, then the amount of radioactivity present in the antibody-bound portion will be inversely related to the quantity of unlabled drug originally added to the reaction mixture. Thus, the greater the amount of unlabeled drug added, the less radiolabeled competitor will be bound to the antibodies. Conversely, the amount of radioactivity present in the reaction mixture from which the antibody-bound portion has been removed will be directly related to the quantity of unlabeled drug originally added to the reaction mixture; i.e. the greater the amount of unlabeled drug added, the more radiolabeled competitor will remain in the reaction mixture from which the antibody-bound portion has been removed.

A standard curve can be produced by employing a range of known concentrations of unlabeled drug in a series of reaction mixtures while holding constant the amount of antibody and radiolabeled competitor employed. The standard curve allows the concentration of drug in an unknown sample to be interpolated from the amount of radioactivity present in the antibody-bound portion of the equilibrated reaction mixture to which it was added.

Thus, it can be seen that the radioimmunoassay of the present invention requires two principal reagents other than the unknown sample of biological fluid to be assayed. These are the radiolabeled competitor of the drug to be assayed, bupropion, and a bupropion-specific antiserum.

Bupropion-specific antisera

Antisera to be used in the radioimmunoassay of the present invention must have high specificity for bupropion, and poor recognition of (i.e., low cross-reaction with) other species which might be present in the biological fluid to be tested, e.g., metabolites of bupropion. According to one aspect of the present invention, suitable immunogens are described, which may be utilized to induce formation of antibodies specific to bupropion and having low recognition of other species in the medium.

Immunogens

The immunogens of the present invention are utilized to induce formation of antibodies specific to bupropion. The immunogens are presented, as by injection with suitable adjuvant, to the immune response system of a host animal. Improved titers can be obtained by a series of injections over a period of time. Suitable host animals include mammals such as horses, goats, guinea pigs and sheep. The preferred host animals are rabbits.

The immunogens of the present invention comprise suitable compounds linked via the aromatic ring or via the side chain ketone, to a suitable carrier material. Suitable carrier materials are known to those skilled in the art and include, for example, proteins; natural or synthetic polymeric materials such as polypeptides, e.g., polylysine and copolymers of amino acids; polysaccharides; and the like. Among the suitable proteins useful in the practice of the present invention are mammalian serum proteins such as, for example, human gamma globulin, human serum albumin, rabbit serum albumin, and bovine gamma globulin. The preferred carrier material is bovine serum albumin (BSA).

While not intending to be bound by theory, it is presently believed that metabolites of bupropion in man involve reduction of the side-chain ketone with or without hydroxylation of the t-butyl group on the nitrogen. Accordingly, the present invention provides methods of making novel bupropion variants which can be linked to a suitable carrier material, preferably via the aromatic ring, thus leaving the side chain available for recognition by the host animal immune system. According to another aspect of the present invention discussed below novel methods are provided for making the drug/carrier conjugate.

The compounds of the present invention for use in immunogen preparation include compounds of Formula I.

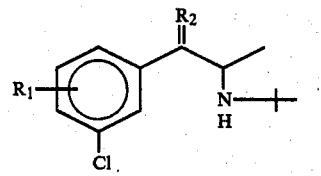

wherein either $R_2$ is oxygen and $R_1$ is $(CH_2)_n-O-(CO)_m-(CH_2)_p-COOH$ where n is an integer from 0 to 5, m is 0 or 1, and p is an integer from 1 to 4; or $R_1$ is hydrogen and $R_2$ is $N-O-(CH_2)_q-COOH$ where q is an integer from 1 to 3.

Included are each enantiomer and any mixture thereof. Preferred compounds include:

α-t-butylamino-3-chloropropiophenonecarboxymethyloxime, (compound 1);

α-t-butylamino-3-chloro-4-carbomethoxypropiophenone, (compound 2); and

α-t-butylamino-3-chloro-4-γ-hydroxypropylpropiophenone hemisuccinate, (compound 3);

each of which has been found to be highly suitable for preparation of immunogens according to the present invention for the purpose of bupropion-specific antisera preparation.

The preferred compound α-t-butylamino-3-chloropropiophenonecarboxymethyloxime, compound 1.

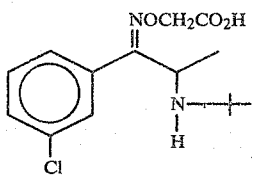

(and suitable analogs and derivatives as would be obvious in view thereof) can be prepared by reaction of bupropion with carboxymethoxylamine hemihydrochloride in the presence of anhydrous sodium acetate in suitable solvent, such as ethanol/water. Suitable variations in the method and alternate reagents will be obvious to one skilled in the art in view of the instant disclosure.

The preferred compound α-t-butylamino-3-chloro-4-carbomethoxypropiophenone, compound 2,

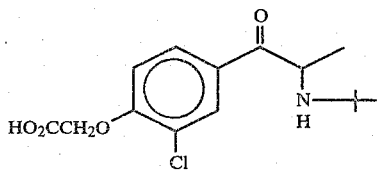

(and suitable analogs and derivatives as would be obvious in view thereof) can be prepared according to known methods by basic hydrolysis of α-t-butylamino-3-chloro-4-carbomethoxypropiophenone methyl ester hydrochloride, compound 4, (or suitable corresponding intermediate) such as by reaction with potassium hydroxide.

Intermediate compound 4 can be prepared from the readily available starting materials o-chlorophenol and propionyl chloride which react with heating to give o-chlorophenyl propionate. Treatment of the product with aluminum chloride produces mixed reaction products including 3-chloro-4-hydroxypropiophenone. To a mixture of 3-chloro-4-hydroxypropiophenone and sodium methoxide dissolved in suitable solvent is added ethyl bromoacetate and reaction at reflux gives ethyl 2-(2-chloro-4-propionylphenoxy) acetate. Subsequent bromination in methanol gives methyl 2-[2-chloro-4-(2-bromopropionyl)-acetate which reacts with t-butylamine to give compound 4. Modifications of the method of synthesis such as selection of suitable and alternate solvents, reaction conditions and reagents, is well within the skill of the art in view of the present disclosure and such modifications do not bring the disclosed method outside the scope of the present invention.

Similarly in view of the present disclosure, it would be within the skill of the art to modify the above method to produce other intermediates for compounds of Formula I. To the extent there is a preferred embodiment of one or more aspects of the method of making compound 4, each is incorporated into the method of Example I.

An alternate method of synthesis of compound 4 is diagramatically illustrated in Synthesis Method A.

The preferred compound α-t-butylamino-3-chloro-4-γ-hydroxypropylpropiophenone hemisuccinate, compound 3,

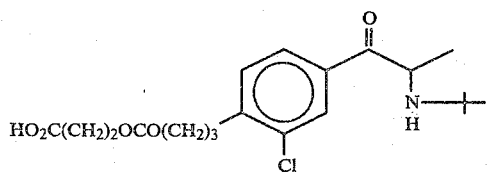

(and suitable analogs and derivatives as would be obvious in view thereof) is prepared by reaction of α-t-butylamino-3-chloro-4-(3-hydroxypropyl)propiophenone hydrochloride three-fourths hydrate, compound 5,

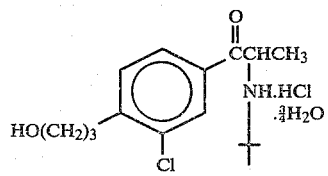

with succinic anhydride in pyridine to form the o-hemisuccinate. Intermediate compound 5 is suitably prepared from readily available starting materials. Accordingly, 3-chloro-4-methyl-benzonitrile, N-bromosuccinimide and benzoyl peroxide react at reflux with illumination to give 2-chloro-4-cyanobenzyl bromide. The product compound can be reacted with diethyl malonate in a solution of sodium in ethanol to give diethyl 2-(2-chloro-4-cyanobenzyl)malonate which, upon subsequent treatment with sodium chloride and water in DMSO produces ethyl 3-(2-chloro-4-cyanophenyl)propanoate. Treatment with suitable base, such as potassium hydroxide and alcoholic solvent gives the corresponding propanoic acid, 3-(2-chloro-4-cyanophenyl)propanoic acid which is then reduced to the corresponding alcohol, such as by treatment with $B_2H_6$ in tetrahydrofuran (THF). A mixture of the alcohol, 3-(2-chloro-4-cyanophenyl)propanol and ethyl magnesium bromide in dry ethyl ether is reacted at reflux to give 3-chloro-4-(3-hydroxypropyl)propiophenone which yields compound 5 upon bromination to α-bromo-3-chloro-4-(3-hydroxypropyl)propiophenone and subsequent reaction of the bromoketone with an excess of t-butylamine in suitable solvent, such as $CH_3CN$.

In view of the present disclosure, it would be within the skill of the art to modify the above method to produce other intermediates for compounds of Formula I and to modify it by selection of alternate suitable solvents, reagents and reaction conditions, none of which modifications take it outside the scope of the present invention. To the extent there is a preferred embodiment of some aspects of this method, each is incorporated into the method of Example II.

The application of the above described method of making compound 3, to other compounds within formula I having the formula

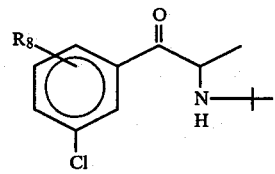

wherein $R_8$ is $(CH_2)_n$—O—$CO(CH_2)_p$—$CO_2H$ where n and p are as defined for formula I, would be within the skill of the art. Thus such compounds can be made by reacting an intermediate compound of formula

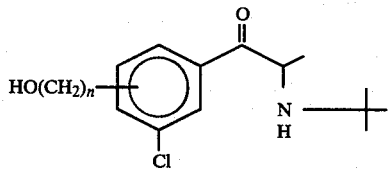

wherein n is as defined for formula I, with

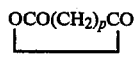

wherein p is as defined for formula I.

The above described method of making compound 2 is readily applied to make other compounds within formula I having the formula

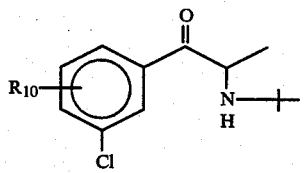

wherein $R_{10}$ is O—$(CH_2)_p$COOH where p is as defined above.

Accordingly, such compounds can be made by basic hydrolysis of an intermediate compound of formula

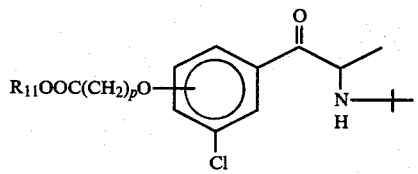

where p is as defined above and $R_{11}$ is alkyl of 1 to 3 carbons. Preferably potassium or sodium hydroxide is used.

Immunogen Preparation

The coupling of a bupropion variant of the present invention to the immunogenic carrier material can be readily accomplished utilizing techniques well known to the skilled in the art. Thus, for example, one suitable technique comprises dissolving the bupropion variant, the carrier material and a suitable coupling agent in suitable inert solvent to react. As discussed above, for assay of human sera or plasma the bupropion variant should be coupled to the carrier material in such a way that regions believed to be affected by metabolic changes in man are presented for ready recognition by the host animal immune system. Thus, coupling is preferably via the aromatic ring. Accordingly, as one aspect of the present invention, there are now disclosed preferred routes to conjugates of the bupropion variants of the present invention such as compounds 2 and 3 disclosed above, linked via the aromatic ring to suitable carrier material. Such conjugates present the bupropion side chain for recognition by the host animal immune system.

A first preferred conjugate comprises compound 2 coupled to BSA using a suitable, water-soluble carbodiimide catalyst. Present understanding suggests that the carbodiimide catalyzes the formation of peptide bonds between the free acid moiety of compound 2 and the $\epsilon$-amino group of lysyl residues of BSA. A preferred carbodiimide is 1-ethyl-3-(3-dimethylaminopropyl)-carbodiimide hydrochloride ("EDC"). In view of the present disclosure, it is within the skill of the art to modify this method of forming the conjugate to apply it to other compounds within formula I or to employ alternate suitable catalyst, none of which modifications take the method outside the scope of the present invention. To the extent there is a preferred embodiment of some aspects of this method, it is incorporated into the method illustrated in Example III.

A second preferred conjugate comprises compound 3 coupled to BSA using the mixed anhydride method. Thus, for example, compound 3 can be reacted with triethlylamine and isobutylchloroformate in dimethylformamide to form the mixed anhydride. Upon addition to BSA in sodium carbonate the desired conjugate is formed. This method is illustrated in Example IV and in view of the present disclosure it is within the skill of the art to apply the method of Example IV to other compounds of formula I. Modifications such as, for example, in the choice of reaction conditions and reagents, will be obvious to the skilled in the art and are not outside the scope of the present invention. To the extent there is a preferred embodiment of some aspects of this method, it is incorporated into the method illustrated in Example IV.

The possibility is seen that ring-hydroxylated metabolites of bupropion could exist in the biological fluid to be assayed. The antisera raised utilizing the immediately above described conjugates might to some extent cross react with such metabolites. While the efficacy of the radioimmunoassay of the present invention would be maintained notwithstanding such possible cross-reaction, there is also provided, as one aspect of the present invention, the preparation of conjugates comprising bupropion variant linked to suitable carrier material, preferably BSA, via the side chain ketone. Utilizing such immunogen provides antisera which would not cross-react substantially with ring-hydroxylated metabolites of bupropion. Such antisera could be expected to cross-react with side-chain alcohol metabolites.

Accordingly, a third preferred conjugate comprises compound 1 coupled to BSA employing a water soluble carbodiimide method. This method is illustrated in Example V.

The radioimmunoassay of the present invention is based on the finding that bupropion will successfully compete with radiolabeled bupropion, or a suitable radiolabeled competitor of bupropion according to the present invention, for binding to antisera raised by presenting a suitable bupropion variant-carrier material conjugate to the immune system of host animals, such as rabbits.

Radiolabeled Bupropion Competitor

Radioactively labeled bupropion or the radioactively labeled bupropion competitors of the present invention can be labeled in the manner well known to the art with any suitable radionuclide. A listing of the radionuclides which are now conventionally in use in reagents and which may be used in this invention are listed in the index of radionuclides found on page 81 of the 1978 edition of the Catalogue of the New England Nuclear Corporation, Boston, Mass., U.S.A. (New England Nuclear, 1977) incorporated herein by reference. Among radionuclides which are preferred in this invention the following may be mentioned: hydrogen-3 (tritium) and the radio isotopes of iodine ($^{123}I$, $^{124}I$, $^{125}I$, $^{126}I$, $^{128}I$, $^{130}I$, $^{131}I$, and $^{132}I$) with $^{125}I$ and $^{3}H$ being preferred from considerations of availability, half life and specific activity and/or the ability of these to be readily detected using a conventional gamma counter usually available in hospitals and sold by Packard Instruments or others. Alternate suitable labeled competitors include those labeled with any other detectable and distinguishing label such as for example, an electron spin resonance group. Other suitable labels include chromophores fluorophors, enzymes, latex particles, and the like. Preferably the label used is an isotope.

The radiolabeled competitors of the present invention are of Formula II:

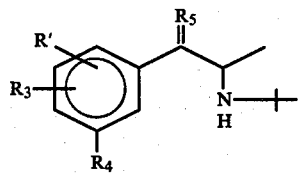

wherein R' is a suitable radioisotope as described above and $R_3$ is hydrogen, $R_4$ is Cl, and $R_5$ is oxygen, or
R' is hydrogen and
either (a) $R_3$ is H and $R_4$ is Cl and $R_5$ is $NO(CH_2)_qCO-X$ where q is as defined for formula I and X is a group having formula III

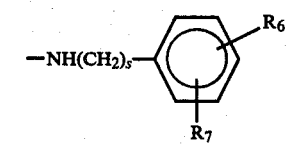

wherein $R_6$ is a suitable radioisotope as described above, $R_7$ is hydroxyl, and s is an integer from 1 to 4; or X is a group having formula III(a)

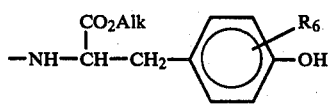

wherein $R_6$ is a suitable radioisotope as described above, and Alk is a lower alkyl containing 1 to 4 carbons;
(b) $R_4$ is Cl, $R_5$ is oxygen, and $R_3$ is $(CH_2)_n-O-(CO)_m-(CH_2)_p-CO-X$ where n, m, and p are as defined for formula I and X is as defined above; or
(c) $R_3$ is hydroxy, $R_5$ is oxygen and $R_4$ is a suitable radioisotope as defined above.

Most preferably, the radiolabeled competitor is selected from

α-t-Butylamino-3-chloropropiophenone-carboxymethyloxime-$^{125}I$-tyramine amide, (Compound 6)

α-t-Butylamino-3-chloro-4-carbomethoxypropiophenone-$^{125}I$-tyramine amide (compound 7)

α-t-Butylamino-3-chloro-4-ε-hydroxypyropylpropiophenone-hemisuccinate-$^{125}I$-tyramine amide (compound 8)

$^{125}I$-α-t-Butylamino-3-iodo-4-hydroxypropiophenone (compound 9)

α-t-Butylamino-3-chloro-2-[$^{3}H$]-propiophenone hydrochloride (compound 10)

In view of the present disclosure, the radiolabeled competitors of the present invention can be made according to methods well known to those skilled in the art. Thus, for the preparation of compound 6, compound 1 can be coupled to tyramine using dicyclohexylcarbodiimide to catalyze the formation of a peptide bond between the free acid of compound 1 and the primary amino group of tyramine. The product is subsequently iodinated in accordance with the Hunter-Greenwood Chloramine-T Method, described in W. M. Hunter and F. C. Greenwood, Nature, 194, 495 (1962) which is incorporated herein by reference in its entirety.

Preferred radiolabeled compound 7 is prepared from compound 2 and tyramine using the mixed anhydride method. Similarly, compound 8 can be prepared from compound 3 using the mixed anhydride method. In each case, the starting reagent is reacted with TEA and isobutyl chlorofomate in DMF to form the mixed anhydride. The reaction mixture is then added to tyramine and the product iodinated as described above.

The application of this method to other compounds of formula III would be within the skill of the art. Thus, compounds within formula III having the formula

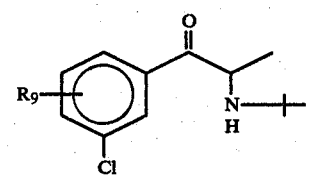

wherein $R_9$ is $(CH_2)_n-O-CO(CH_2)_pCO-X$ where n, p and X are as defined above, can be made by reacting a compound of formula 1 with trialkylamine and alkyl haloformate to form the mixed anhydride and subsequently adding the reaction mixture to $HOC_6H_4(CH_2)_sNH_2$ wherein s is as defined above. The product is subsequently iodinated, preferably with $^{125}I$. The trialkyamine preferably comprises an alkyl moiety of about 1 to 4 carbon and the alkyl moiety of alkyl haloformate preferably has 1 to 7 carbon. Triethylamine and isobutyl chloroformate are most preferred.

TEA is triethylamine and DMF in dimethylformamide. DMSO is dimethylsulfoxide.

Similarly, compounds within formula II having the formula

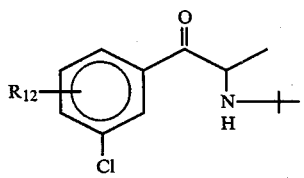

wherein $R_{12}$ is $O—(CH_2)_pCO—X$ where p is as defined above and X is III or IIIa

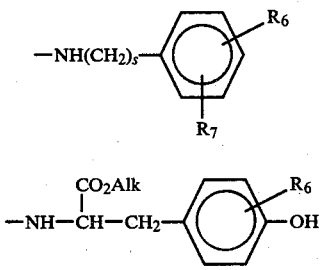

where $R_6$, $R_7$, s and Alk are as defined above, can be made by reacting a compound of formula 1 with trialkylamine alkyl halofomate, as those terms were used above, to form the mixed anhydride. Subsequently adding the reaction mixture to $HOC_6H_4(CH_2)_sNH_2$ where s is as defined above or to $HOC_6H_4CH_2CH-(CO_2Alk)NH_2$ where Alk is as defined above and then iodinating preferably with $^{125}I$ gives the desired radiolabeled competitor compound.

Compound 9 can be prepared by demethylation of α-t-butylamino-4-methoxypropiophenone

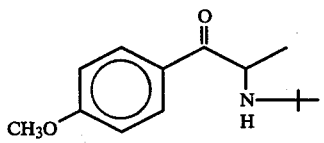

followed by iodination of the phenolic product.

Compound 10 is $^3H$ labeled bupropion and can be prepared as shown herein.

The Bupropion Radioimmunoassay Procedure

Preferably for high specificity, the antiserum is in each case raised to a bupropion variant which corresponds to the radiolabeled competitor used in the assay. Thus, radiolabeled competitor compound 6, is preferably used in conjunction with anti-(α-t-butylamino-3-choropropiophenone-carboxymethyloxime-BSA) sera, ("anti-compound 1 sera"). Compound 7 and compound 8 are each preferably used with antisera raised to an immunogen wherein the bupropion variant is linked to the carrier material via the aromatic ring. Thus, each is preferably used with either anti-compound 2 sera or with anti-compound 3 sera. Radiolabeled competitor compounds 9 and 10 also are each used preferably with antisera raised to immunogens linked via the aromatic ring to the carrier material. Competition between the bupropion, if any, present in the biological fluid being assayed and the radiolabeled competitor proceeds in such a manner that equilibrium is achieved corresponding to the relative concentration of bupropion and radiolabeled competitor in the assay mixture.

The present invention is also based in part upon the discovery that once the competition of bupropion and radiolabeled competitor has proceeded for the desired time, preferably to equilibrium, the antibody bound portion of the drug and competitor can be separated from the free portion of the drug and competitor. Following such separation, the amount of radioactivity in the antibody bound portion gives a measure of the amount of unlabeled bupropion which was present in the test mixture.

According to the preferred radioimmunoassay of the present invention, a standard curve is constructed by running the assay on two or more, preferably four to 8 solutions, each having a different known bupropion concentration within a suitable concentration range. In addition, an assay is run with only the radiolabeled competitor without the addition of bupropion, such that the maximum possible binding can be quantified. The assay for each standard solution can be expressed as a percent of maximum binding and plotted on a graph against the concentration of bupropion in the assayed sample. The value obtained upon assay of the unknown biological sample expressed as percent of maximum binding can then be used to interpolate its bupropion concentration from the standard curve.

Preferably, duplicate measures of standard bupropion solutions, preferably in blank plasma, are prepared such as by pipetting equal amounts of each standard solution into plastic tubes. In addition, duplicate "nonspecific binding tubes," that is tubes which will not receive antisera, and duplicate "maximum binding tubes," that is tubes which will not receive unlabeled bupropion, also each receive a like measure of blank plasma. While it is indicated that each sample is assayed in duplicate, this is merely preferred for greater accuracy and the average value for each pair is used. If desired, the assay may even be performed with triplicate samples. After being placed in an ice bath, all tubes receive a portion of radiolabeled competitor and subsequently all tubes, except non-specific binding tubes, receive anti-bupropion serum raised to an appropriate immunogen of the present invention. Preferably, the radiolabeled competitor and antiserum are in suitable assay buffer, such as phosphate buffered isotonic saline containing EDTA and gelatin. The non-specific binding tubes receive blank assay buffer.

Following incubation, when the bupropion and the competing radiolabeled competitor in the assay mixture have substantially reached equilibrium, antibody-bound radiolabeled competitor is separated from the free portion thereof by any suitable means such as are known to the skilled in the art. In one preferred method a complex is formed between protein in the assay mixture and another added protein by incubation, for example, overnight at ambient temperature. The complex precipitates out and can be centrifuged to a pellet for measurement of radioactivity. Alternately, ammonium sulfate can be added to get a faster precipitation.

However, a novel and useful feature of the radioimmunoassay of the present invention is the ethanol precipitation of antibody-bound $^{125}I$-bupropion competitor from the equilibrium assay mixture. In this novel and preferred method for quick precipitation, the assay mixture must be kept ice-cold, such as by immersion in an ice bath. Absolute ethanol is added to the ice-cold mixture and quickly precipitates all the protein in the assay mixture. The precipitate can be pelletized and thus use of ethanol precipitation is significantly advantageous in allowing quantitation of $^{125}I$ in the protein pellets.

The quantitation of the antibody-bound radiolabeled competitor such as, for example, by beta of gamma radiation count of the antibody-bound $^{3}H$ or $^{125}I$ labeled competitor respectively minus the average count obtained for the non-specific binding tubes, is expressed as a percentage of the quantitation of the maximum binding tubes (also minus the average count obtained for the non-specific binding tubes). Using the results obtained for the tubes containing standard bupropion solution samples, a standard curve can be constructed as already described. The assay procedure will be further explained by illustration in the examples.

The antisera raised to the above described ring functionalized immunogens have been found to provide excellent specificity. Cross reaction with the bupropion metabolites believed to occur in man, has been found to be of a low level.

The novel immunogens and antibodies of the present invention may be utilized in conjunction with conventional additives, buffers, stabilizers, diluents, or in combination with other physiologically active or inactive substances.

As one aspect of the present invention a kit is provided, such as for a mercantile unit, for practicing the radioimmunoassay of the present invention. Such kit comprises at least one container, such as, for example, a test tube, containing bupropion-specific antisera and bupropion competitor. In one embodiment, the antisera, presented, for example, in freeze dried form, is adhered to a first portion of the container and bupropion competitor is adhered to a second, separate portion of the container. In such embodiment, any suitable adhesive means can be used, such as, for example, a water soluble adherent which will not interfer with the binding of bupropion or of the competitor to the antisera. Alternately, each reagent can be presented individually, each in one or more separate containers. The kit can also comprise, in the same or different container(s), standard amount(s) of bupropion, antisera and competitor. This would be preferred for example, where a standard curve is to be constructed.

The figures are useful to an understanding of the present invention.

Figure 1:
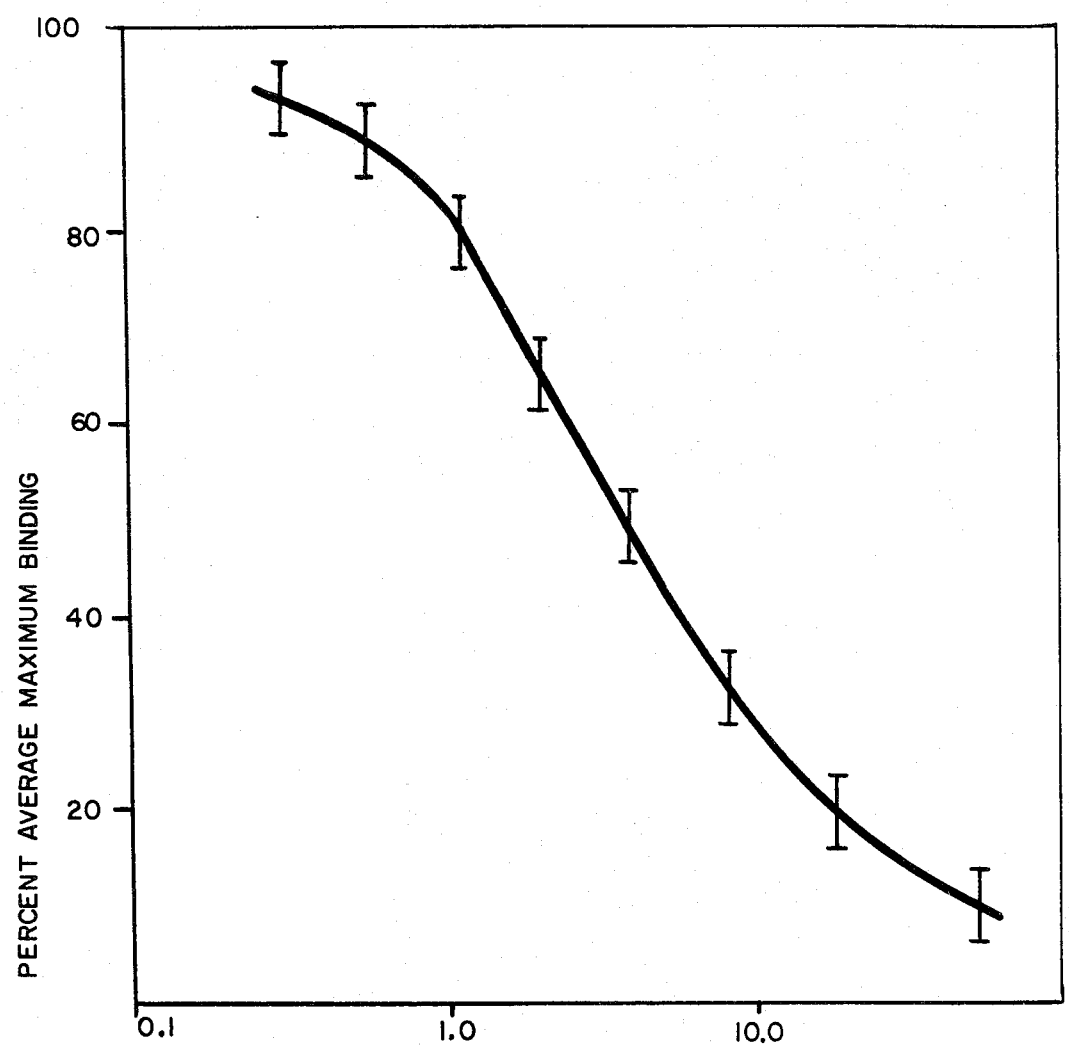
FIG. 1 is a standard curve showing inhibition of the binding of radiolabeled competitor as a function of bupropion concentration.

From the foregoing it will be appreciated that the present invention provides:

(1) A novel radioimmunoassay method for the detection and/or quantitation of bupropion and immunologically active metabolites thereof in a body fluid;
(2) Novel immunogens to raise bupropion-specific antibodies useful in the radioimmunoassay;
(3) Antisera comprising bupropion specific antibodies raised by the novel immunogens of the present invention;
(4) Novel radioactive isotope labelled competitors of bupropion for use in the radioimmunoassay;
(5) Novel compounds which can be coupled to a suitable immunogenic material to make the immunogens of the present invention.
(6) Novel methods of making the immunogens of the present invention.
(7) Novel methods of making the radioactive isotope labelled competitors of the present invention.
(8) A kit, of at least one container of bupropion-specific antibodies and bupropion competitior for practicing the radioimmunoassay of the present invention.

Whenever alkyl or a group comprising alkyl is used herein, the alkyl moiety thereof contains 1 to 6 carbon atoms unless otherwise specified. As used herein t-butylamino means tert-butylamino.

EXAMPLE I

Preparation of α-t-butylamino-3-chloro-4-carbomethoxypropiophenone methyl ester hydrochloride, compound 4

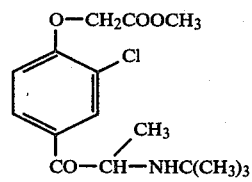

A. o-Chlorophenyl propionate

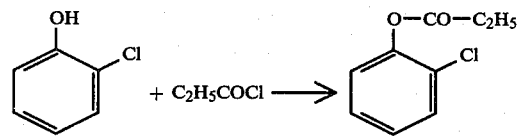

o-Chlorophenol (64 g, 0.5 mole) and propionyl chloride (50 g, 0.55 mole) were mixed at room temperature and then heated at 100° C. (steam bath) for 2-3 hrs. Hydrogen chloride gas was evolved. After 2-3 hrs the reaction mixture was distilled in vacuo and gave 78.8 g (86%) of o-chlorophenyl propionate, bp 11 $_{mm}$=111° C.

Anal for $C_9H_9O_2Cl$ M.W. 184.63
Calcd: C, 58.54; H, 4.91,
Found: C, 58.31; H, 4.88.

B. 3-chloro-4-hydroxpropiophenone

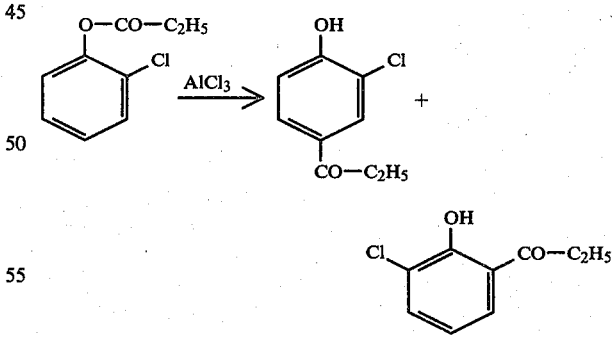

To anhydrous aluminium chloride (37 g, 0.27 mole), o-chlorophenyl propionate (24.8 g, 0.13 mole) was added rapidly (vigorous reaction). The reaction mixture was heated at 120°-130° C. (in a metal bath) for 30-45 min. After cooling, the aluminum chloride reaction mixture was decomposed with a mixture of ice and concentrated HCl. Tie solid organic material was filtered off by suction, and was washed with much cold water giving 18-20 g of solids. This product was recrystallized several times from ethyl acetate-hexane giving two parts: (1) 13-14 g insoluble in hexane and (2) 5-6 g from evaporation of the ethyl acetate-hexane filtrates.

The 13-14 g of hexane insoluble material was recrystallized several times from mixtures of ethyl acetate and hexane. It was charcoaled while in the hot ethyl acetate solution and gave finally 3-chloro-4-hydroxypropiophenone (12 g, 48.4%) mp 114°-115° C. (D. Chakravarti and B. Majurndar., *J. Indian Chem. Soc.*, 16, 151-159 (1939) reported a mp of 80° C. for this product)

Anal for $C_9H_9O_2Cl$ M.W. 184.63
Calcd: C, 58.54; H 4.91
Found: C, 58.41; H 4.76.

The material from the ethyl acetate-hexane soluble filtrate after several recrystallizations from hexane gave 2-hydroxy-3-chloropropiophenone (4.3 g, 17.3%) mp 42°-45° C.

Anal for $C_9H_9O_2Cl$ M.W. 184.63
Calcd: C, 58.54; H 4.91,
Found: C, 58.42; H 4.76.

C. Ethyl 2-(2-chloro-4-propionylphenoxy) acetate

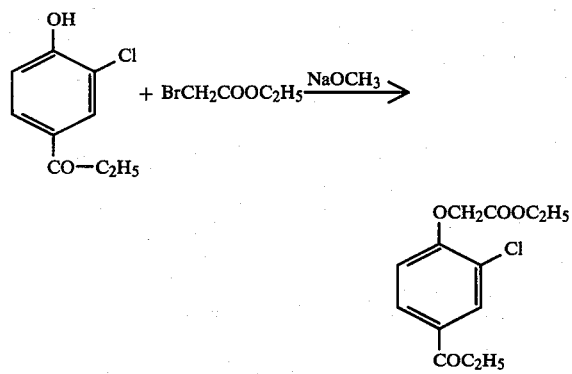

Sodium methoxide (2.5 g, 0.045 mole) was dissolved in absolute ethanol (40 ml) 3-Chloro-4-hydroxy-propiophenone (7.4 g, 0.04 mole) was added and the mixture warmed for 1-2 minutes. Ethyl bromoacetate (7.3 g, 0.44 mole) was added, and the reaction mixture was refluxed at 100° C. (steam bath) for 2-3 hrs. Most of the ethanol was evaporated, ice and water were added and the mixture was neutralized to pH 4-5 with dilute HCl. Cooling and scratching of the flask initiated crystallization. The resulting solid was dissolved in excess ether, washed 3× with 5% NaOH, then with water. The ethereal solution was dried over sodium sulfate (anhydrous), filtered and evaporated and gave 9-10 g of crude material. Several recrystallizations from ethyl acetate gave ethyl 2-(2-chloro-4-propionylphenoxy)acetate (8.3 g, 77%), mp 129°-130° C.

Anal for $C_{13}H_{15}O_4Cl$ M.W. 270.72,
Calcd: C, 57.67; H 5.59,
Found: C, 57.67; H 5.43.

D. Methyl 2-[2-chloro-4-(2-bromopropionyl)-phenoxy]acetate.

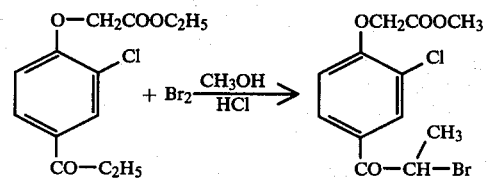

Ethyl-2-(2-chloro-4-propionylphenoxy)acetate(4 g) was dissolved in methanol (40-50 ml). HCl (2 drops, conc) was added, followed by the dropwise addition over 5-10 minutes of bromine (2.62 g, 0.016 mole). After the bromine addition was complete the mixture was heated on a steam bath for 15-30 minutes allowing much of the solvent to evaporate. The residue was washed with cold water and the remaining solid recrystallized several times from hexane to give methyl 2-[2-chloro-4-(2-bromopropionyl)phenoxy]acetate (4.6 g, 90%, mp 63°-65° C.

Anal for $C_{12}H_{12}O_4ClBr$ M.W. 335.69,
Calcd: C, 42.93; H 3.60,
Found: C, 43.83; H 3.46.

E. Methyl 2-[2-chloro-4-(2-t-butylaminopropionyl)-phenoxy]acetate hydrochloride

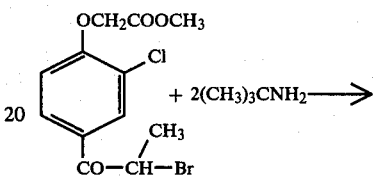

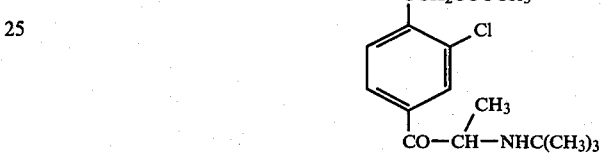

To methyl 2-[2-chloro-4-(2-bromopropionyl)-phenoxy]acetate (3.3 g, 0.01 mole) in acetonitrile (20 ml) t-butylamine (3.3 g, 0.044 mole) was added, and the reaction mixture was left overnight at 40° C. (near a warm steam bath). In the morning the mixture was heated on a steam bath, allowing solvent and excess amine to evaporate (to dryness). The residue was treated with cold water and NaOH to pH 11 and extracted quickly with ether. The ethereal solution was dried over anhydrous sodium sulfate, filtered, and evaporated to remove ether and any traces of t-butylamine. The residue was redissolved in ether and precipitated as the hydrochloride salt by the addition of a little alcoholic HCl. The white crystalline solid was recrystallized two times from mixtures of methanol-ethyl acetate-ether to give methyl 2-[2-chloro-4-(2-t-butylaminopropionyl)phenoxy]acetate hydrochloride (2.5 g, 68.5%), mp 213°-215° C.

Anal for $C_{16}H_{23}NO_4Cl_2$ M.W. 364.29
Calcd: C, 52.76; H, 6.36; N, 3.8; O, 17.57; Cl, 19.47
Found: C, 52.48; H, 6.42; N, 3.71; Cl, 19.36.

EXAMPLE II

Preparation of α-t-butylamino-3-chloro-4-γ-hydroxypropylpropiophenone hemisuccinate, compound 3

A. 2-Chloro-4-cyanobenzyl bromide

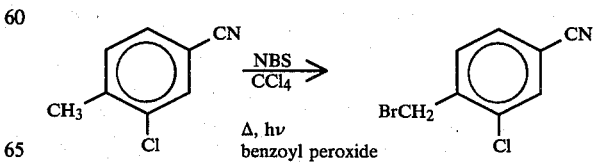

A mixture of 3-chloro-4-methyl-benzonitrile (30.0 g, 0.2 mol), N-bromosuccinimide (36.0 g, 0.21 mol) and benzoyl peroxide (100 mg) in 600 mL of CCl₄ was refluxed with illumination for 72 h. N-Bromosuccinimide (5.0 g) was added and the reaction was continued for an additional 24 h. The mixture was cooled, filtered and evaporated. Recrystallization from heptane gave pure 2-chloro-4-cyanobenzyl bromide: yield 24.5 g; mp 83°–85° C. Anal. calcd for C₈H₅BrClN; C, 41.69; H, 2.19; N, 6.07. Found: C, 41.48; H, 1.80; N, 5.76.

B. Diethyl 2-(2-chloro-4-cyanobenzyl)malonate

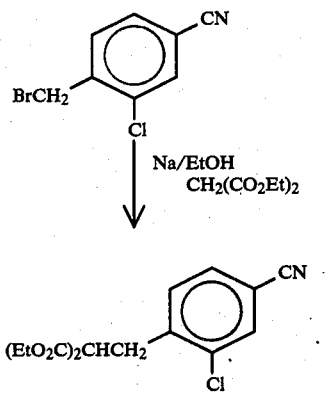

To sodium (2.0 g, 0.09 mol) dissolved in ethanol was added diethylmalonate (15.7 g, 0.1 mol) followed by 2-chloro-4-cyanobenzyl bromide (20.0 g, 0.09 mol). The mixture was refluxed for 3.5 h. The solvent was evaporated and 120 mL of water and 3.6 mL of concentrated hydrochloric acid was added to the residue. Separation and distillation gave diethyl 2-(2-chloro-4-cyanobenzyl)malonate as an oil: 12.5 g; bp 140°–142° C. (0.1 mm Hg). Anal. calcd for C₁₅H₁₆ClNO₄: C, 58.16; H, 5.21; N, 4.52. Found: C, 58.07; H, 5.22; N, 4.52.

C. Ethyl 3-(2-chloro-4-cyanophenyl)propanoate

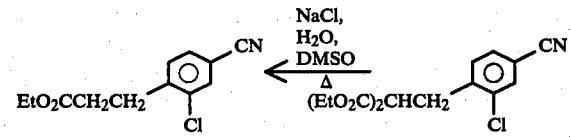

A mixture of diethyl 2-(2-chloro-4-cyanobenzyl)malonate (9.0 g, 0.03 mol), sodium chloride (2.12 g, 0.04 mol), and water (0.86 g 0.05 mol) in 30 mL of DMSO was heated to 135° C. and then the temperature was gradually raised to 170° C. over a 3 h period. The mixture was diluted with water and extracted with ether. Evaporation and distillation gave ethyl 3-(2-chloro-4-cyanophenyl)propanoate as an oil: 5.8 g; bp 138°–140° C. (0.1 mm Hg) Anal. calcd for C₁₂H₁₂ClNO₂: C, 60.64; H, 5.09; N, 5.89. Found: C, 60.48; H, 5.08; N, 5.84.

D. 3-(2-Chloro-4-cyanophenyl)propanoic acid

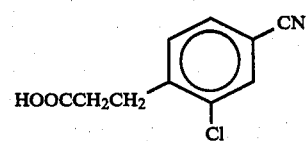

A mixture of ethyl 3-(chloro-4-cyanophenyl)propanoate (33.0 g, 0.14 mol), KOH (6.27 g, 0.11 mol) and 95% ethanol (109 mL) was warmed at 40° C. for 1 h. The mixture was neutralized and evaporated to dryness. The residue was dissolved in 5% NaHCO₃ and washed with EtOAc. Acidification and filtration gave crystalline 3-(2-chloro-4-cyanophenyl)propanoic acid: 18.4 g; mp 127°–219° C.

E. 3-(2-Chloro-4-cyanophenyl)propanol

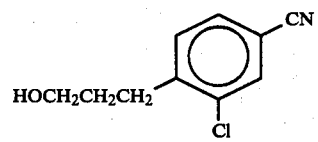

To 3-(2-chloro-4-cyanophenyl)-propanoic acid (14.3 g, 0.068 mol) in 70 mL of dry THF at −18° C. was added B₂H₆(72 ml, 0.068 mol) in THF. The mixture was stirred at room temperature overnight. After addition of water, the layers were separated and the aqueous phase was extracted with ether. Evaporation and distillation gave 3-(2-chloro-4-cyanophenyl)propanol as an oil: 11.0 g; bp 55°–60° C. (0.005 mm Hg). Anal. calcd for C₁₀H₁₀ClNO: C, 61.39; H, 5.15; N, 7.16. Found: C, 61.02; H, 5.19; N, 6.76.

F. 3-Chloro-4-(3-hydroxypropyl)propiophenone

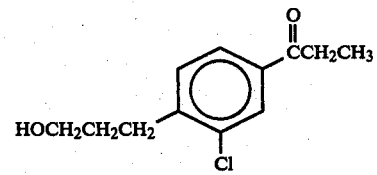

A mixture of 3-(2-chloro-4-cyanophenyl)propanol (18.0 g, 0.09 mol) and ethyl magnesium bromide (36.8 g, 0.276 mol) in dry ethyl ether was refluxed for 4 h. After quenching the reaction with 150 mL of 15% HCl, the layers were separated and the aqueous layer was extracted with ethyl acetate. Evaporation and recrystallization from ethyl ether-pentane gave 3-chloro-4-(3-hydroxpropyl)propiophenone: 7.9 g; mp 46°–48° C.

G. α-t-Butylamino-3-chloro-4-(3-hydroxpropyl)propiophenone hydrochloride three-fourths hydrate

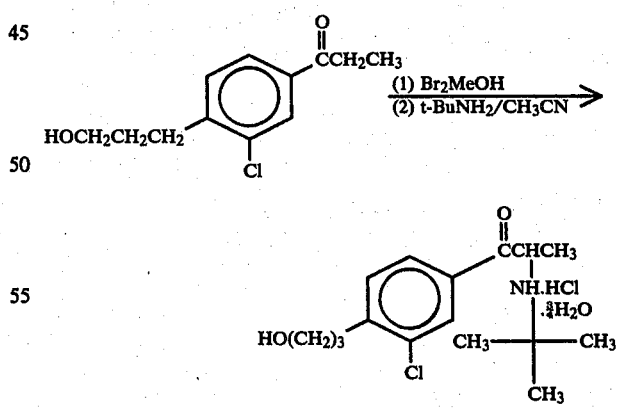

A mixture of 3-chloro-4-(3-hydroxypropyl)propiophenone (7.7 g, 0.03 mol) and bromine (5.7 g, 0.04 mol) in dry methanol was stirred at room temperature overnight. Evaporation and distillation gave α-bromo-3-chloro-4-(3-hydroxypropyl)propiophenone: 9.6 g; bp 102°–105° C. (0.005 mm Hg). The bromoketone was stirred overnight with an excess of tert-butylamine in CH₃CN at room temperature. The crude α-t- butylamino-3-chloro-4-(3-hydroxypropyl)propiophenone was isolated and converted to the hydrochloride salt: yield 1.25 g; mp 203°–205° C. dec. Anal. Called for $C_{16}H_{24}ClNO_2 \cdot HCl \cdot \frac{3}{4}H_2O$: C, 55.22; H, 7.68; N, 4.02. Found: C, 55.14; H, 7.39; N, 4.16.

EXAMPLE III

IMMUNOGEN PREPARATION

α-t-butylamino-3-chloro-4-carbomethoxypropiophenone-BSA. (Compound 2-BSA)

Compound 2 (25.4 mg; 0.088 mmole) reacted with BSA (40 mg; 0.00057 mmole) and EDC (25 mg) in 15 ml 10% dioxane/water at pH 5.7 overnight at 25° C. The reaction mixture was pressure dialyzed vs. deionized water, concentrated by ultrafiltration and the immunogen lyophilized overnight.

EXAMPLE IV

α-t-butylamino-3-chloro-4-γ-hydroxypropylpropiophenone hemisuccinate-BSA (compound 3-BSA)

Compound 3 (25.5 mg; 0.064 mmole) reacted with triethylamine (TEA, 9.8 mg; 0.097 mmole) and isobutylchloroformate (9.8 mg; 0.072 mmole) in 1 ml dimethylformamide (DMF) at 4° C. for 30 minutes to form the mixed anhydride. This reaction mixture was slowly added to a well-stirred solution of BSA (30 mg; 0.00043 mmole) in 4 ml 0.1 $\overline{M}$ sodium carbonate at 4° C. and allowed to react overnight. The reaction mixture was pressure dialyzed and lyophilized as in Example III.

EXAMPLE V

α-t-butylamino-3-chloropropionphenone-carboxymethyloxime-BSA, (compound 1-BSA)

Compound 1 was coupled to bovine serum albumin (BSA) using a water-soluble carbodiimide to catalyze the formation of peptide bonds between the free acid moiety of II and the ε-amino groups of lysyl residues of BSA. Compound 1 (25 mg; 0.080 mmole) was reacted with BSA (40 mg; 0.00057 mmole), and 1-ethyl-3(3-dimethylaminopropyl)-carbodiimide (EDC, 25 mg) in 15 ml 10% dioxane/water at pH 5.7 overnight at 25° C. The reaction mixture was pressure dialyzed vs deionized water, concentrated by ultra-filtration and the immunogen lyophilized overnight.

EXAMPLE VI

α-t-butylamino-3-chloropropiophenone-carboxymethyloxime-$^{125}$I-tyramine amide, compound 6

Compound 1 was coupled to tyramine using dicyclohexylcarbodiimide to catalyze the formation of a peptide bond between the free acid of II and the primary amino group of tyramine. Compound 1 (15 mg; 0.048 mmole) reacted with tyramine (free base, 13 mg; 0.096 mmole) and dicyclohexylcarbodiimide (DCC; 19 mg) in 2 ml dry dioxane at pH 5 overnight at 25° C. The product was purified by TLC, characterized spectrally and subsequently iodinated (Hunter-Greenwood Chloramine-T Method).

EXAMPLE VII

α-t-butylamino-3-chloro-4-carbomethoxypropiophenone-$^{125}$I-tyramine amide, compound 7

Compound 2 was coupled to tyramine using the mixed anhydride method. Compound 2 (25 mg; 0.076 mmole) was reacted with TEA (9.8 mg; 0.097 mmole) and isobutyl chloroformate (9.8 mg; 0.072 mmole) in 1 ml DMF at 4° C. for 30 minutes to form the mixed anhydride. The reaction mixture was slowly added to a well-stirred solution of tyramine (free base, 10 mg; 0.073 mmole) in 1 ml DMF at 4° C. and allowed to react overnight to yield the phenolic product. The product was purified by TLC, characterized spectrally and subsequently iodinated as in Example VI.

EXAMPLE VIII

α-t-butylamino-3-chloro-4-γ-hydroxypropylpropiophenonehemisuccinate-$^{125}$I-tyramine amide, compound 8

Compound 3 was coupled to tyramine using the mixed anhydride method of Example VII. This product was purified by TLC and subsequently iodinated as described in Example VI.

EXAMPLE IX $^{125}$I-α-t-butylamino-3-iodo-4-hydroxypropiophenone, compound 9 α-t-butylamino-4-methoxypropiophenone hydrochloride (20.6 mg; 0.076 mmole) was suspended in 1 ml dry methylene chloride and cooled to −80° C. in an acetone-dry ice bath. Boron tribromide (41.9 mg; 0.167 mmole) was added, the reaction mixture was protected from moisture with a calcium chloride drying tube, and the reaction was allowed to proceed overnight, during which time the temperature rose to 25° C. The reaction mixture was shaken with one volume methylene chloride (containing 0.02% water impurity) to liberate the product. The product was purified by TLC and subsequently iodinated as described in Example VI.

EXAMPLE X

RIA of Bupropion in Plasma Using $^3$H Bupropion

Samples of six standard solutions of bupropion in blank plasma having concentrations of 0.39 to 50 ng/ml) are pipetted (0.1 ml each) in duplicate into 12×75 mm plastic tubes. Duplicate non-specific binding (no antibody) and maximum binding tubes (no unlabeled bupropion) receive 0.1 ml blank plasma. Spiked plasma controls at several concentrations of (e.g., 1.0, 10.0, and 100 ng/ml) and plasma samples for assay (diluted into the standard range with blank plasma if necessary) are assayed in duplicate. After being placed in an ice bath, all tubes receive (in order) 0.2 ml $^3$H bupropion (416 pg. containing approximately 10$^4$ cpm) and 0.7 ml anti-bupropion serum (raised to a ring-functionalized immunogen according to the present invention) (at pre-determined dilutions such that approximately 40% of the $^3$H bupropion added is bound), both in assay buffer (0.05 M phosphate-buffered isotonic saline, containing 0.01 M EDTA and 0.1% gelatin, pH 7.0). Non-specific binding tubes receive 0.7 ml assay buffer.) Following incubation either at 25° C. for 2 hours or overnight at 4° C., bound and free $^3$H bupropion are separated by incubation for 10 min at 0° C. with 0.5 ml ice-cold dextran-coated charcoal solution (0.25% dextran, 5 mg/ml charcoal, in assay buffer) followed by centrifugation for 10 minutes at 4° C. (5000 rpm) to pellet the charcoal. The supernatants, containing antibody-bound $^3$H bupropion are carefully decanted into liquid scintillation cocktail for quantitation of $^3$H. After counts (minus average nonspecific binding cpm) are expressed as percentages of average maximum binding cpm, bupropion concentrations in plasma samples and spiked controls are read from a standard curve (log concentration vs percent average maximum binding).

EXAMPLE XI

The procedure of Example X has been applied to a study of bupropion (supplied as Wellbatrin, produced by Burroughs Wellcome Co.) pharmacokinetics in plasma after oral administration of 200 mg bupropion-HCl (in two 100 mg tablets) to four normal male subjects. Venous blood samples were collected at various times following dosing, and concentrations in plasma samples determined as described. The assay standard curve obtained by this method (±interassay standard deviation, N=8) is shown in FIG. 1. Spiked controls (at 1, 10 and 100 ng/ml) run with 8 separate assays gave interassay values of 0.89±0.11 (S.D.), 10.35±0.60, and 92.72±5.02, respectively. Plots of elapsed time vs plasma bupropion concentration for each subject were made. Using these data, various pharmacokinetic parameters were calculated using the C-strip and NONLIN computer programs. The mean elimination half-life, maximum plasma bupropion concentration and time to reach this maximum concentration were 2.9±0.4 (S.D.) hours, 217±37 ng/ml, and 1.5±0.4 hours, respectively.

EXAMPLES XIII-XVII

RIA of Bupropion using $^{125}$I-labeled Bupropion Competitors

Figure 2:
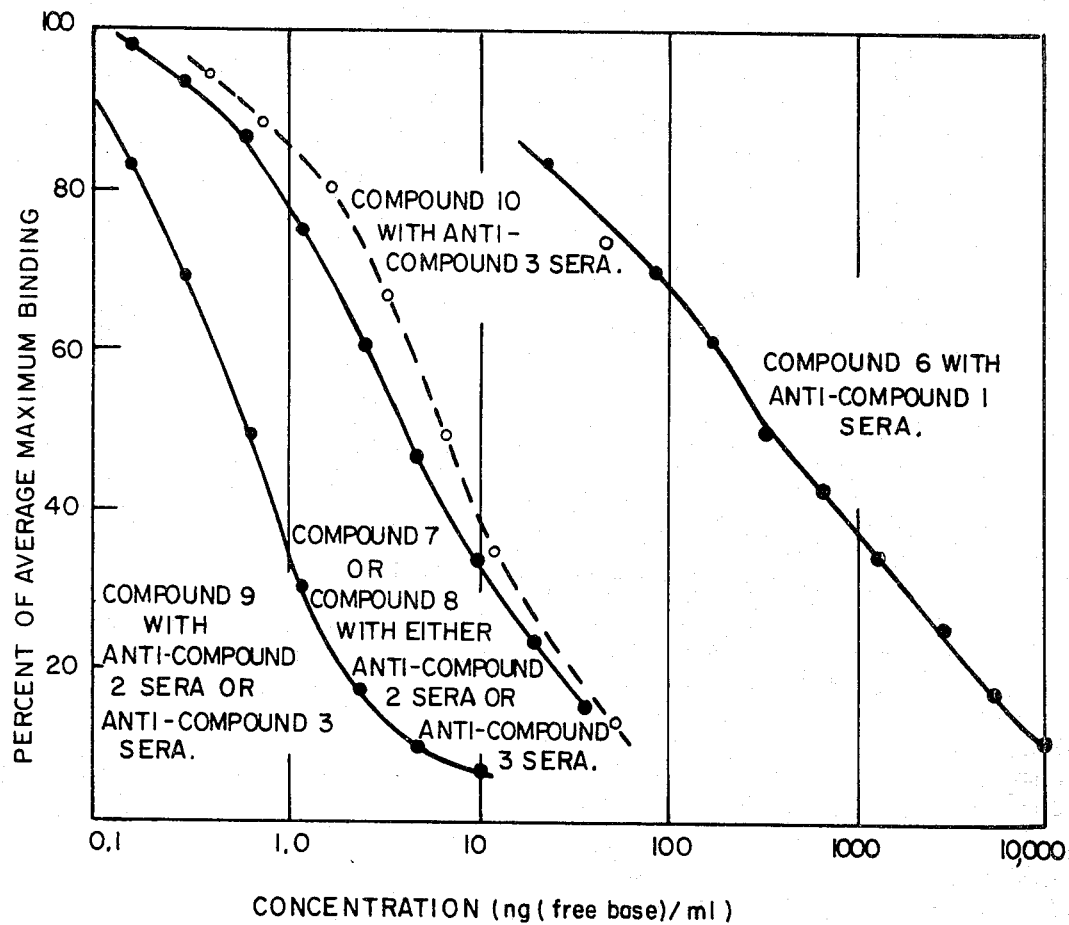
FIG. 2 shows standard curves obtained using certain $^{125}I$ iodinated bupropion competitors and antisera according to the present invention.

RIA's have been run according to the method of Example X utilizing $^{125}$I labeled bupropion competitors of the present invention in conjunction with antisera obtained following immunization with immunogens of the present invention. Compound 6 was used in conjunction with anti-compound 1 sera. Compounds 7, 8 and 9 were each used with anti-compound 2 sera, and with anti-compound 3 sera. Following the ethanol precipitation of antibody-bound $^{125}$I-bupropion competitor at equilibrium, $^{125}$I in the protein pellets was quantified. FIG. 2 shows standard curves obtained with the various iodinated competitors.

It can be seen that compound 9, in conjunction with either antisera produces RIA's approximately ten times more sensitive than the compound 10 ($^{3}$H bupropion) assay system. Substitution of 7 or 8 yields sensitivity approximately equal to that obtained with the compound 10 system. The anti-compound 1 sera and compound 6, which preferably are used for RIA only in conjunction with each other, produced the least sensitive RIA. However, by virtue of derivatization via the ketone, these antisera are believed to exhibit much less cross reaction with ring-hydroxylated metabolites, albeit at the expense of specificity for changes in structure at the ketone.

EXAMPLE XVIII

Preparation of α-t-butylamino-3-chloro-2-tritiopropiophenone hydrochloride (Compound 10)

A. 2-(3-Chloro-2-tritiophenyl)-4,4-dimethyl-2-oxazoline 2-(3-Chlorophenyl)-4,4-dimethyl-2-oxazoline was prepared from 3-chlorobenzoic acid by reaction with thionyl chloride to give 3-chlorobenzoylchloride, reaction of this acid chloride with 2-amino-2-methylpropanol to give the amide and cyclization of the amide with thionyl chloride followed by neutralization with dilute sodium hydroxide to give 2-(3-chlorophenyl)-4,4-dimethyl-2-oxazoline.

The oxazoline (419.2 mg) in dry ether (15 ml) was cooled to −78° C. and tert-butyllithium (2.0 m moles) in pentane (1.12 ml) was added under nitrogen with stirring. Stirring was continued at −78° C. for 4½ hours. Solvent-free T$_2$O (0.5 ml, 90% isotopic purity) was added, and the solution was allowed to slowly warm to room temperature and stirred overnight. The solution was dried over anhydrous magnesium sulfate and filtered, and the solvent was removed in vacuo to give an orange oil. Purification was achieved by column chromatography on silica (12.6 g) packed as a chloroform slurry. The crude reaction product was added to the column as a chloroform solution. Elution was with chloroformethyl acetate (3:1 V/V). Fractions containing the radiolabeled oxazoline were combined. Solvent removal in vacuo gave 2-(3-chloro-2-tritiophenyl)-4,4-dimethyl-2-oxazoline (334 mg, 79%) as a yellow oil. Nmr and mass spectral data confirmed the structure; the radiolabel was about 90% of theoretical.

B. 2-(3-Chloro-2-tritiophenyl)-4,4-dimethyl-2-oxazoline N-Methylfluorosulfonate

To 2-(3-chloro-2-tritiophenyl)-4,4-dimethyl-2-oxazoline (670.7 mg) in dry benzene (7 ml) under nitrogen was added methane fluorosulfonate (1.4 g). The mixture was stirred overnight at room temperature under nitrogen. The white precipitate was collected under nitrogen, washed with benzene (1×10 ml) and ether (2×10 ml) and dried to give 2-(3-chloro-2-tritiophenyl)-4,4-dimethyl-2-oxazoline N-methylfluorosulfonate in greater than 90% yield.

C. 2-(3-Chloro-2-tritiophenyl)-2-ethyl-4,4-dimethyl-N-methyloxazolidine

To the dry 2-(3-chloro-2-tritiophenyl)-4,4-dimethyl-2-oxazoline N-methylfluorosulfonate from step C in dry THF (15 ml) under nitrogen was rapidly added ethylmagnesium chloride (8.0 m moles) in ether (2.7 ml). The mixture was stirred for 1 hour at room temperature and then poured into an ice-water mixture (75 ml) with stirring. The resulting suspension was extracted with ether (1×100 ml followed by 1×50 ml). The combined ether extracts were washed with water 1×50 ml) and dried over anhydrous magnesium sulfate. Filtration and removal of solvent in vacuo gave 2-(3-chloro-2-tritiophenyl)-2-ethyl-4,4-dimethyl-N-methyloxazolidine (83% yield) as a yellow oil.

D. 3-Chloro-2-tritiopropiophenone

A mixture of the crude oxazolidine from step C (670.5 mg) and oxalic acid (475.6 mg) in water (10 ml) was heated at reflux for 1 hour and then cooled to room temperature. Additional water (15 ml) was added, and the product was extracted with ether (2×15 ml). The ether layer was washed with 5% potassium bicarbonate solution (2×15 ml) and dried over anhydrous magnesium sulfate. Solvent was removed in vacuo to give 3-chloro-2-tritiopropiophenone (405 mg).

E. α-t-Butylamino-3-chloro-2-tritiopropiophenone hydrochloride

Following the procedure of U.S. Pat. No. 3,819,706 incorporated herein by reference, 3-chloro-2-tritiopropiophenone was brominated and the α-bromo product treated with tert-butylamine to give α-t-butylamino-3-chloro-2-tritiopropiophenone which was isolated as the hydrochloride (43% yield).

SYNTHESIS METHOD A

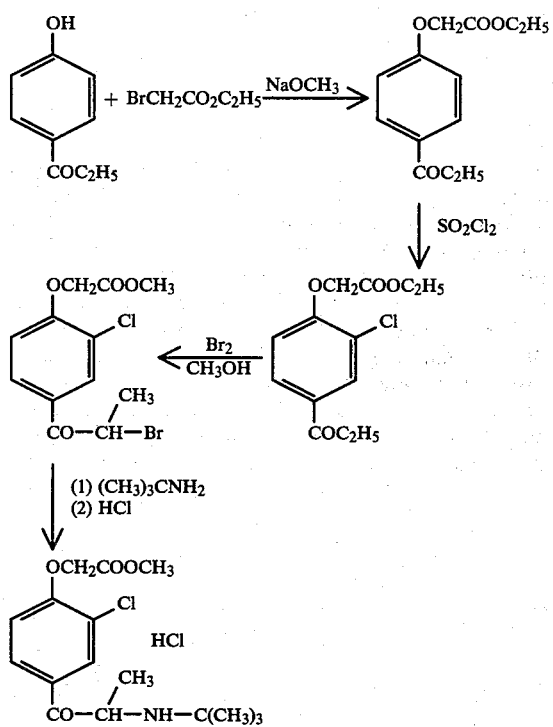

I claim:
1. A compound of the formula

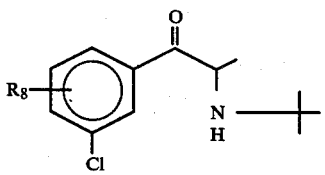

wherein $R_8$ is $(CH_2)_n$—O—$CO(CH_2)_p$—$CO_2H$ where n is an integer from 1 to 5 and p is an integer from 1 to 4.

2. The compound according to claim 1 wherein $R_8$ is at the 4-position.

3. The compound according to claim 2 which is α-t-butylamino-3-chloro-4-γ-hydroxypropylpropiophenone hemisuccinate.

4. The method of making a compound of claim 1 comprising reacting an intermediate compound of formula

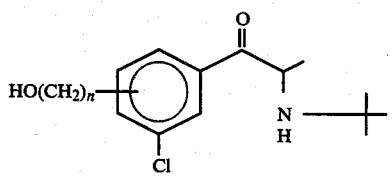

wherein n is an defined in claim 1, with

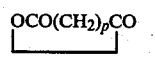

wherein p is as defined in claim 1.

5. A method according to claim 4 of making the compound of claim 3 comprising reacting intermediate compound

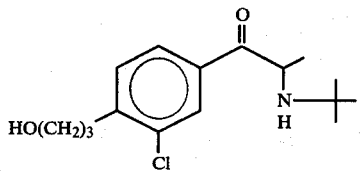

with succinic anhydride.

6. A compound of the formula

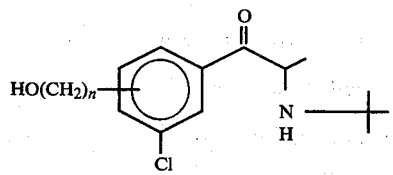

wherein n is an integer from 1 to 5.

7. The compound according to claim 6 which is

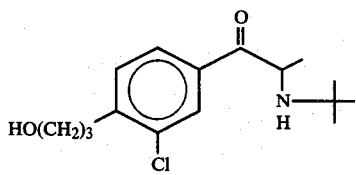

8. A compound of the formula

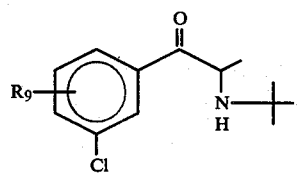

wherein $R_9$ is
$(CH_2)_n$—O—$CO(CH_2)pCO$—X where n and p are as defined for claim 1 and X is

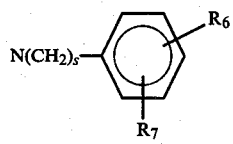

wherein $R_6$ is a radioactive nuclide, $R_7$ is hydroxyl, and s is an integer from 1 to 4.

9. A compound according to claim 8 wherein said radioactive nuclide is selected from $^3H$ and $^{125}I$.

10. A compound according to claim 8 in which $R_9$ is γ-hydroxyproplpropiophenone-hemisuccinate-$^{125}I$-tyramine amide.

11. A compound according to claim 10 in which $R_9$ is at the 4-position.

12. A method of making a compound of claim 8 comprising reacting a compound of claim 1 with trialkylamino, the alkyl moiety of which has 1 to 4 carbons and alkyl haloformate, the alkyl moiety of which has 1 to 3 carbons, and subsequently adding the reaction mixture to

HOC<sub>6</sub>H<sub>4</sub>(CH<sub>2</sub>)<sub>s</sub>NH<sub>2</sub> wherein s is as defined in claim 7, and subsequently $^{125}$I iodinating the product.

13. A method according to claim 12 wherein said trialkylamine is triethylamine, said alkyl haloformate is isobutyl chloroformate and the reaction mixture is subsequently added to tyramine.

14. An immunogen comprising a conjugate comprising a compound of formula:

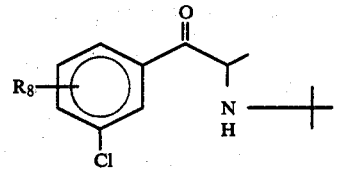

wherein R<sub>8</sub> is as defined for claim 1, coupled to a suitable immunogenic carrier material.

15. An immunogen according to claim 14 wherein the immunogenic carrier material is bovine serum albumin.

16. An immunogen according to claim 15 in which R<sub>8</sub> is γ-hydroxypropylpropiophenone-hemisuccinate and said carrier material is bovine serum albumin.

17. An immunogen according to claim 16 in which R<sub>8</sub> is at the 4-position.

18. A method of making an immunogen according to claim 14 comprising reacting said compound, said immunogenic carrier material and a suitable coupling agent.

* * * * *